United States Patent
Vuong et al.

(10) Patent No.: US 7,522,295 B2
(45) Date of Patent: Apr. 21, 2009

(54) CONSECUTIVE MEASUREMENT OF STRUCTURES FORMED ON A SEMICONDUCTOR WAFER USING A POLARIZED REFLECTOMETER

(75) Inventors: Vi Vuong, Fremont, CA (US); Junwei Bao, Palo Alto, CA (US); Manuel Madriaga, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 42 days.

(21) Appl. No.: 11/594,497

(22) Filed: Nov. 7, 2006

(65) Prior Publication Data

US 2008/0106728 A1   May 8, 2008

(51) Int. Cl.
     G01B 11/04   (2006.01)
(52) U.S. Cl. ...................................... 356/636
(58) Field of Classification Search ................. 356/636
     See application file for complete search history.

(56) References Cited

U.S. PATENT DOCUMENTS

| | | | |
|---|---|---|---|
| 6,785,638 | B2 | 8/2004 | Niu et al. |
| 6,842,261 | B2 * | 1/2005 | Bao et al. ............... 356/636 |
| 6,891,626 | B2 | 5/2005 | Niu et al. |
| 6,943,900 | B2 | 9/2005 | Niu et al. |
| 7,333,200 | B2 * | 2/2008 | Sezginer et al. ........... 356/401 |
| 2002/0135875 | A1 * | 9/2002 | Niu et al. ................ 359/564 |
| 2002/0148782 | A1 | 10/2002 | Raymond ................. 356/616 |
| 2002/0158193 | A1 * | 10/2002 | Sezginer et al. ......... 250/237 G |
| 2004/0017574 | A1 | 1/2004 | Vuong et al. |
| 2004/0169861 | A1 * | 9/2004 | Mieher et al. ............. 356/400 |
| 2004/0267397 | A1 | 12/2004 | Doddi et al. |
| 2005/0209816 | A1 | 9/2005 | Vuong et al. |

OTHER PUBLICATIONS

Li, L. (1996) "Formulation and comparison of two recursive matrix algorithms for modeling layered diffraction gratings," *Journal of the Optical Society of America A* 13:1024-1035.
Haykin, S. (1999). *Neural Networks*. 2nd edition, M. Horton ed., Prentice Hall: Upper Saddle River, New Jersey, 9 pages (Table of Contents).
Ausschnitt, C. P. (Feb. 23, 2004). "A New Approach to Pattern Metrology," *Proceedings of SPIE* 5375:51-55.
U.S. Appl. No. 11/371,752, filed Mar. 8, 2006 for Vuong et al.

* cited by examiner

*Primary Examiner*—Roy M Punnoose
*Assistant Examiner*—Isiaka O Akanbi
(74) *Attorney, Agent, or Firm*—Morrison & Foerster LLP

(57) ABSTRACT

Structures formed on a semiconductor wafer are consecutively measured by obtaining first and second measured diffraction signals of a first structure and a second structure formed abutting the first structure. The first and second measured diffraction signals were consecutively measured using a polarized reflectometer. The first measured diffraction signal is compared to a first simulated diffraction signal generated using a profile model of the first structure. The profile model has profile parameters that characterize geometries of the first structure. One or more features of the first structure are determined based on the comparison. The second measured diffraction signal is converted to a converted diffraction signal. The converted diffraction signal is compared to the first simulated diffraction signal or a second simulated diffraction signal generated using the same profile model as the first simulated diffraction signal. One or more features of the second structure are determined based on the comparison.

26 Claims, 8 Drawing Sheets

CONSECUTIVE MEASUREMENT OF STRUCTURES FORMED ON A SEMICONDUCTOR WAFER USING A POLARIZED REFLECTOMETER

BACKGROUND

1. Field

The present application generally relates to optical metrology of a structure formed on a semiconductor wafer, and, more particularly to consecutive measurement of structures formed on a semiconductor wafer using a polarized reflectometer.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional optical metrology system, the diffraction signal collected from illuminating the periodic grating (the measured-diffraction signal) is compared to a library of simulated-diffraction signals. Each simulated-diffraction signal in the library is associated with a hypothetical profile. When a match is made between the measured-diffraction signal and one of the simulated-diffraction signals in the library, the hypothetical profile associated with the simulated-diffraction signal is presumed to represent the actual profile of the periodic grating.

The library of simulated-diffraction signals can be generated using a rigorous method, such as rigorous coupled wave analysis (RCWA). More particularly, in the diffraction modeling technique, a simulated-diffraction signal is calculated based, in part, on solving Maxwell's equations. Calculating the simulated diffraction signal involves performing a large number of complex calculations, which can be time consuming and costly. Typically, a number of optical metrology measurements are performed for a number of sites in a wafer. The number of wafers that can be processed in a time period is proportional to the speed of determining the structure profile from the measured diffraction signals.

SUMMARY

In one exemplary embodiment, structures formed on a semiconductor wafer are consecutively measured by obtaining first and second measured diffraction signals of a first structure and a second structure formed abutting the first structure. The first and second measured diffraction signals were consecutively measured using a polarized reflectometer. The first measured diffraction signal is compared to a first simulated diffraction signal generated using a profile model of the first structure. The profile model has profile parameters that characterize geometries of the first structure. One or more features of the first structure are determined based on the comparison. The second measured diffraction signal is converted to a converted diffraction signal. The converted diffraction signal is compared to the first simulated diffraction signal or a second simulated diffraction signal generated using the same profile model as the first simulated diffraction signal. One or more features of the second structure are determined based on the comparison.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the term structure when it is not qualified refers to a patterned structure.

1. Optical Metrology Tools

Figure 1A:
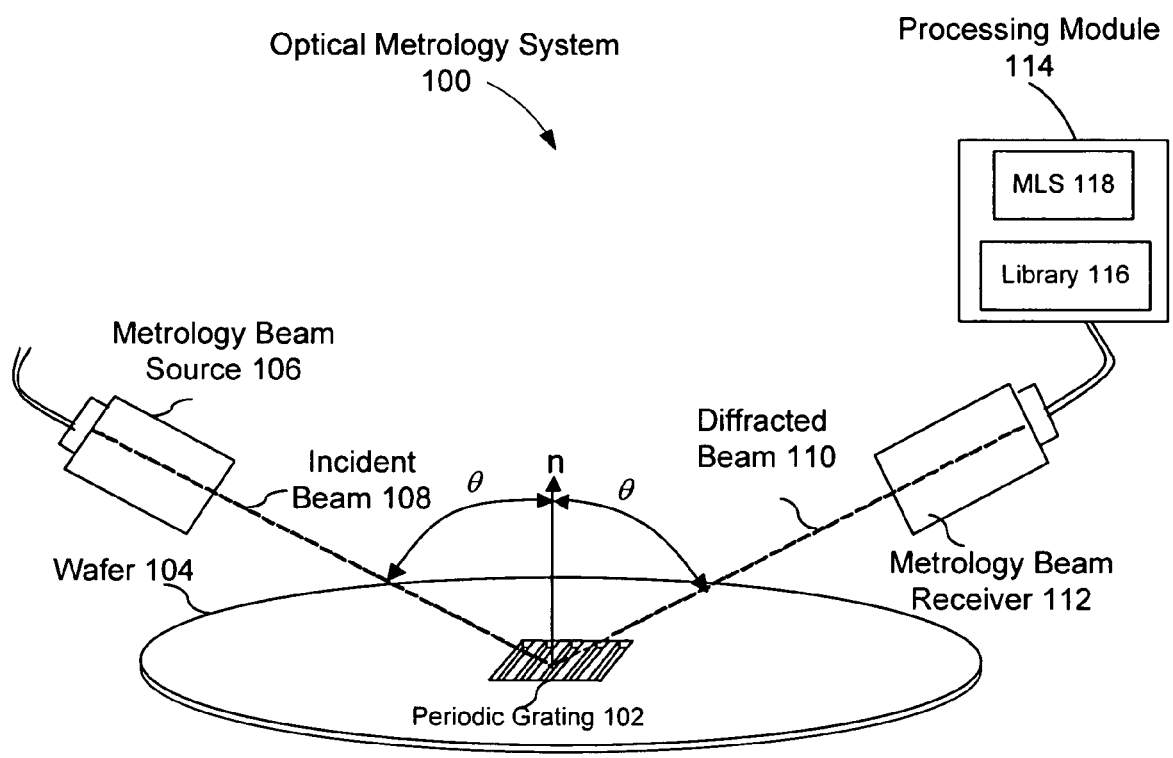
FIG. 1A is an architectural diagram illustrating an exemplary embodiment where optical metrology can be utilized to determine the profiles of structures on a semiconductor wafer.

With reference to FIG. 1A, an optical metrology system 100 can be used to examine and analyze a structure formed on a semiconductor wafer 104. For example, optical metrology system 100 can be used to determine one or more features of a periodic grating 102 formed on wafer 104. As described earlier, periodic grating 102 can be formed in a test pad on wafer 104, such as adjacent to a die formed on wafer 104. Periodic grating 102 can be formed in a scribe line and/or an area of the die that does not interfere with the operation of the die.

As depicted in FIG. 1A, optical metrology system 100 can include a photometric device with a source 106 and a detector 112. Periodic grating 102 is illuminated by an illumination beam 108 from source 106. The illumination beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal and is received by detector 112. Detector 112 converts the diffracted beam 110 into a measured diffraction signal, which can include reflectance, tan ($\Psi$), cos($\Delta$), Fourier coefficients, and the like. Although a zero-order diffraction signal is depicted in FIG. 1A, it should be recognized that non-zero orders can also be used. For example, see Ausschnitt, Christopher P., "A New Approach to Pattern Metrology," Proc. SPIE 5375-7, Feb. 23, 2004, pp 1-15, which is incorporated herein by reference in its entirety.

Optical metrology system 100 also includes a processing module 114 configured to receive the measured diffraction signal and analyze the measured diffraction signal. Processing module 114 is configured to determine one or more features of the periodic grating using any number of methods which provide a best matching diffraction signal to the measured diffraction signal. These methods are described below and include a library-based process or a regression based process using simulated diffraction signals obtained by rigorous coupled wave analysis and machine learning systems.

2. Library-Based Process of Determining Feature of Structure

In a library-based process of determining one or more features of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1A, in one exemplary embodiment, after obtaining a measured diffraction signal, processing module 114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing the profile of periodic grating 102 using a profile model. The profile model is characterized using a set of profile parameters. The set of profile parameters of the profile model are varied to generate hypothetical profiles of varying shapes and dimensions. The process of characterizing the actual profile of periodic grating 102 using the profile model and a set of profile parameters can be referred to as parameterizing.

Figure 2A:
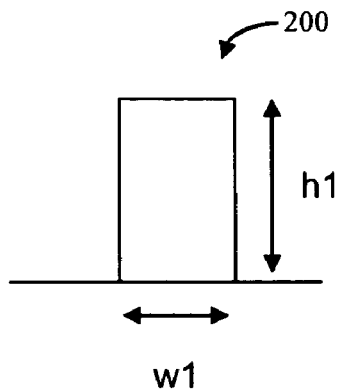
FIGS. 2A-2E depict various exemplary profile models.
Figure 2B:
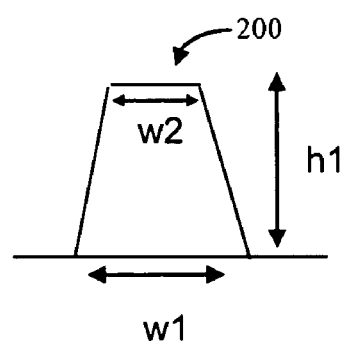
Figure 2C:
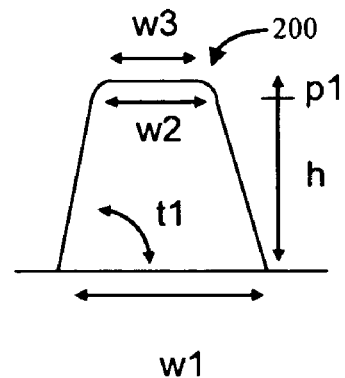
Figure 2D:
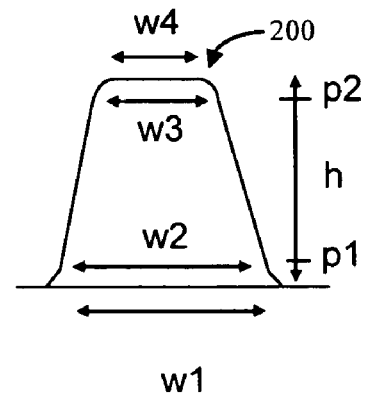
Figure 2E:
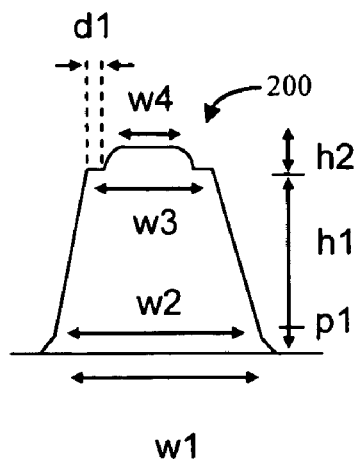

For example, as depicted in FIG. 2A, assume that profile model 200 can be characterized by profile parameters h1 and w1 that define its height and width, respectively. As depicted in FIGS. 2B to 2E, additional shapes and features of profile model 200 can be characterized by increasing the number of profile parameters. For example, as depicted in FIG. 2B, profile model 200 can be characterized by profile parameters h1, w1, and w2 that define its height, bottom width, and top width, respectively. Note that the width of profile model 200 can be referred to as the critical dimension (CD). For example, in FIG. 2B, profile parameter w1 and w2 can be described as defining the bottom CD (BCD) and top CD (TCD), respectively, of profile model 200.

As described above, the set of hypothetical profiles stored in library 116 (FIG. 1A) can be generated by varying the profile parameters that characterize the profile model. For example, with reference to FIG. 2B, by varying profile parameters h1, w1, and w2, hypothetical profiles of varying shapes and dimensions can be generated. Note that one, two, or all three profile parameters can be varied relative to one another.

With reference again to FIG. 1A, the number of hypothetical profiles and corresponding simulated diffraction signals in the set of hypothetical profiles and simulated diffraction signals stored in library 116 (i.e;, the resolution and/or range of library 116) depends, in part, on the range over which the profile parameters and the increment at which the profile parameters are varied. The hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-Based Process of Determining Feature of Structure

In a regression-based process of determining one or more features of a structure, the measured diffraction signal is compared to a simulated diffraction signal (i.e., a trial diffraction signal). The simulated diffraction signal is generated prior to the comparison using a set of profile parameters (i.e., trial profile parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of profile parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1A, the processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is not within a preset or matching criterion, then processing module 114 can iteratively generate another simulated diffraction signal for another hypothetical profile. The subsequently generated simulated diffraction signal can be generated using an optimization algorithm, such as global optimization techniques, which includes simulated annealing, and local optimization techniques, which includes steepest descent algorithm.

The simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analysis

As described above, simulated diffraction signals are generated to be compared to measured diffraction signals. As will be described below, the simulated diffraction signals can be generated by applying Maxwell's equations and using a numerical analysis technique to solve Maxwell's equations. It should be noted, however, that various numerical analysis techniques, including variations of RCWA, can be used.

In general, RCWA involves dividing a hypothetical profile into a number of sections, slices, or slabs (hereafter simply referred to as sections). For each section of the hypothetical profile, a system of coupled differential equations is generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the hypothetical profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

5. Machine Learning Systems

The simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In one exemplary embodiment, the simulated diffraction signals in a library of diffraction signals, such as library 116 (FIG. 1A), used in a library-based process are generated using a MLS. For example, a set of hypothetical profiles can be provided as inputs to the MLS to produce a set of simulated diffraction signals as outputs from the MLS. The set of hypothetical profiles and set of simulated diffraction signals are stored in the library.

In another exemplary embodiment, the simulated diffractions used in regression-based process are generated using a MLS, such as MLS 118 (FIG. 1A). For example, an initial hypothetical profile can be provided as an input to the MLS to produce an initial simulated diffraction signal as an output from the MLS. If the initial simulated diffraction signal does not match the measured diffraction signal, another hypothetical profile can be provided as an additional input to the MLS to produce another simulated diffraction signal.

FIG. 1A depicts processing module 114 having both a library 116 and MLS 118. It should be recognized, however, that processing module 114 can have either library 116 or MLS 118 rather than both. For example, if processing module 114 only uses a library-based process, MLS 118 can be omitted. Alternatively, if processing module 114 only uses a regression-based process, library 116 can be omitted. Note, however, a regression-based process can include storing hypothetical profiles and simulated diffraction signals generated during the regression process in a library, such as library 116.

Figure 1B:
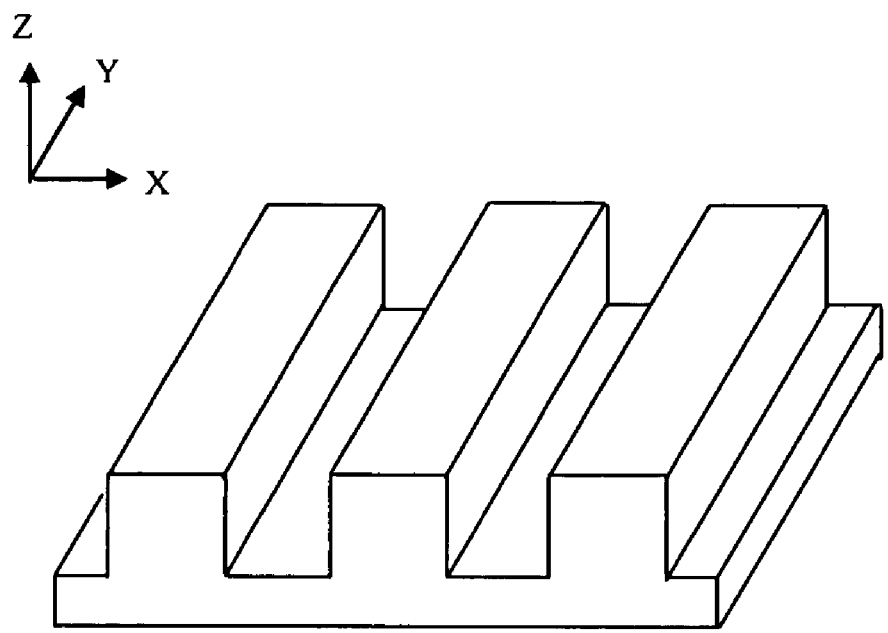
FIG. 1B depicts an exemplary one-dimension repeating structure.

The term "one-dimension structure" is used herein to refer to a structure having a profile that varies only in one dimension. For example, FIG. 1B depicts a periodic grating having a profile that varies only in one dimension (i.e., the x-direction). The profile of the periodic grating depicted in FIG. 1B varies in the z-direction as a function of the x-direction. However, the profile of the periodic grating depicted in FIG. 1B is assumed to be substantially uniform or continuous in the y-direction.

Figure 1C:
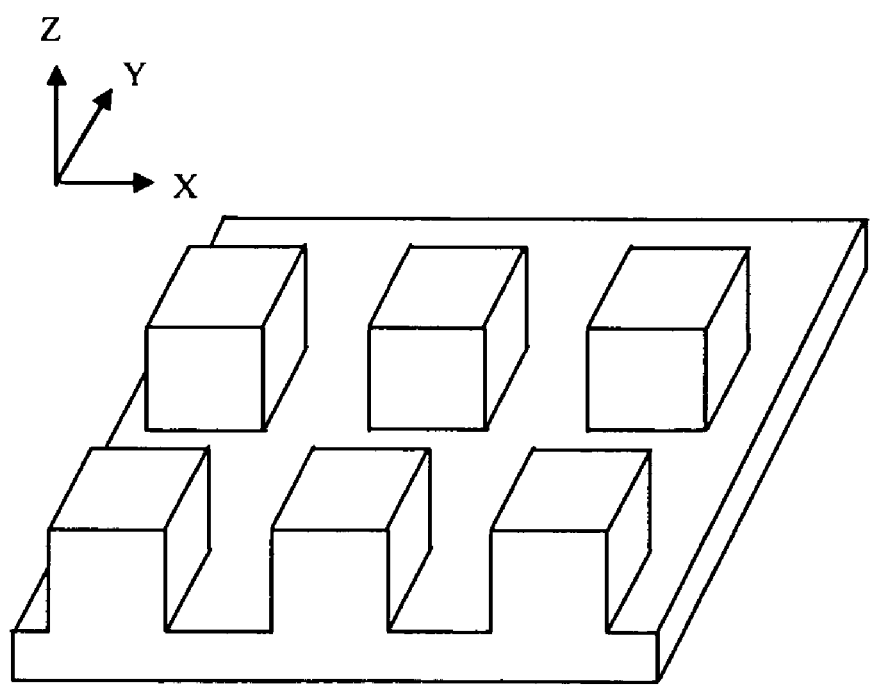
FIG. 1C depicts an exemplary two-dimension repeating structure.

The term "two-dimension structure" is used herein to refer to a structure having a profile that varies in two-dimensions. For example, FIG. 1C depicts a periodic grating having a profile that varies in two dimensions (i.e., the x-direction and the y-direction). The profile of the periodic grating depicted in FIG. 1C varies in the z-direction.

Figure 3A:
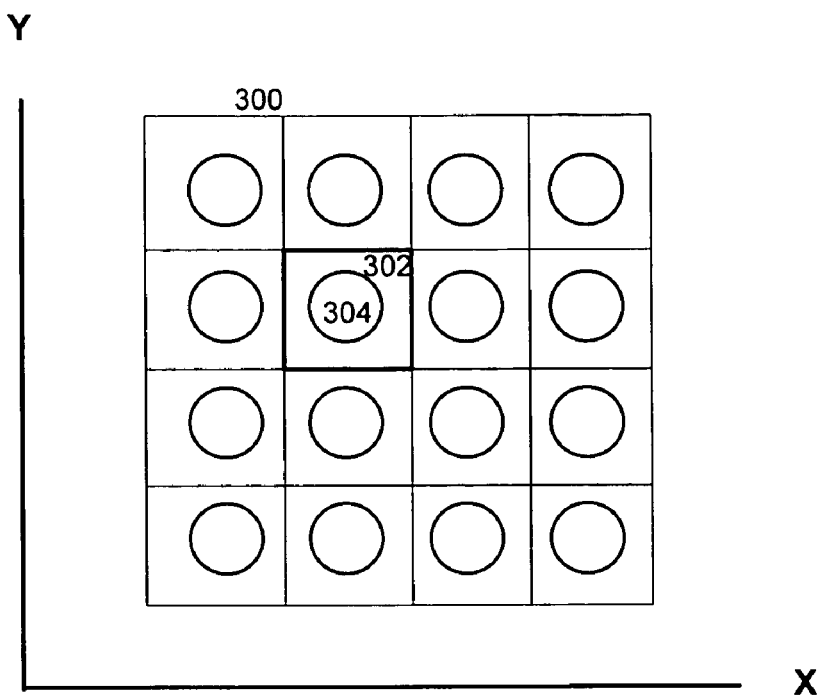
FIG. 3A depicts exemplary orthogonal grid of unit cells of a two-dimension repeating structure.

Discussion for FIGS. 3A, 3B, and 3C below describe the characterization of two-dimension repeating structures for profile modeling. FIG. 3A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of one or more pairs of shapes within a unit cell. Furthermore, the features may have a variety of shapes and may be concave or convex features or a combination of concave and convex features. Referring to FIG. 3A, the repeating structure 300 comprises unit cells with holes arranged in an orthogonal manner. Unit cell 302 includes all the features and components inside the unit cell 302, primarily comprising a hole 304 substantially in the center of the unit cell 302.

Figure 3B:
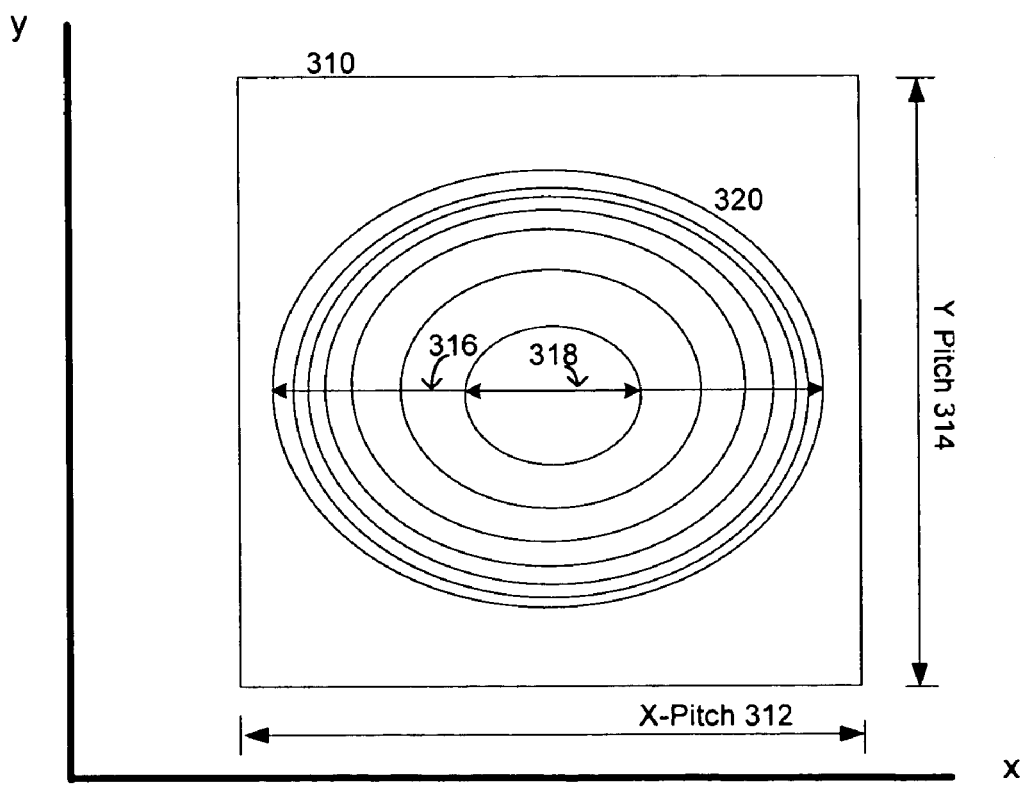
FIG. 3B depicts a top-view of a two-dimension repeating structure.

FIG. 3B depicts a top-view of a two-dimension repeating structure. Unit cell 310 includes a concave elliptical hole. FIG. 3B shows a unit cell 310 with a feature 320 that comprises an elliptical hole wherein the dimensions become progressively smaller until the bottom of the hole. Profile parameters used to characterize the structure includes the X-pitch 312 and the Y-pitch 314. In addition, the major axis of the ellipse 316 that represents the top of the feature 320 and the major axis of the ellipse 318 that represents the bottom of the feature 320 may be used to characterize the feature 320. Furthermore, any intermediate major axis between the top and bottom of the feature may also be used as well as any minor axis of the top, intermediate, or bottom ellipse, (not shown).

Figure 3C:
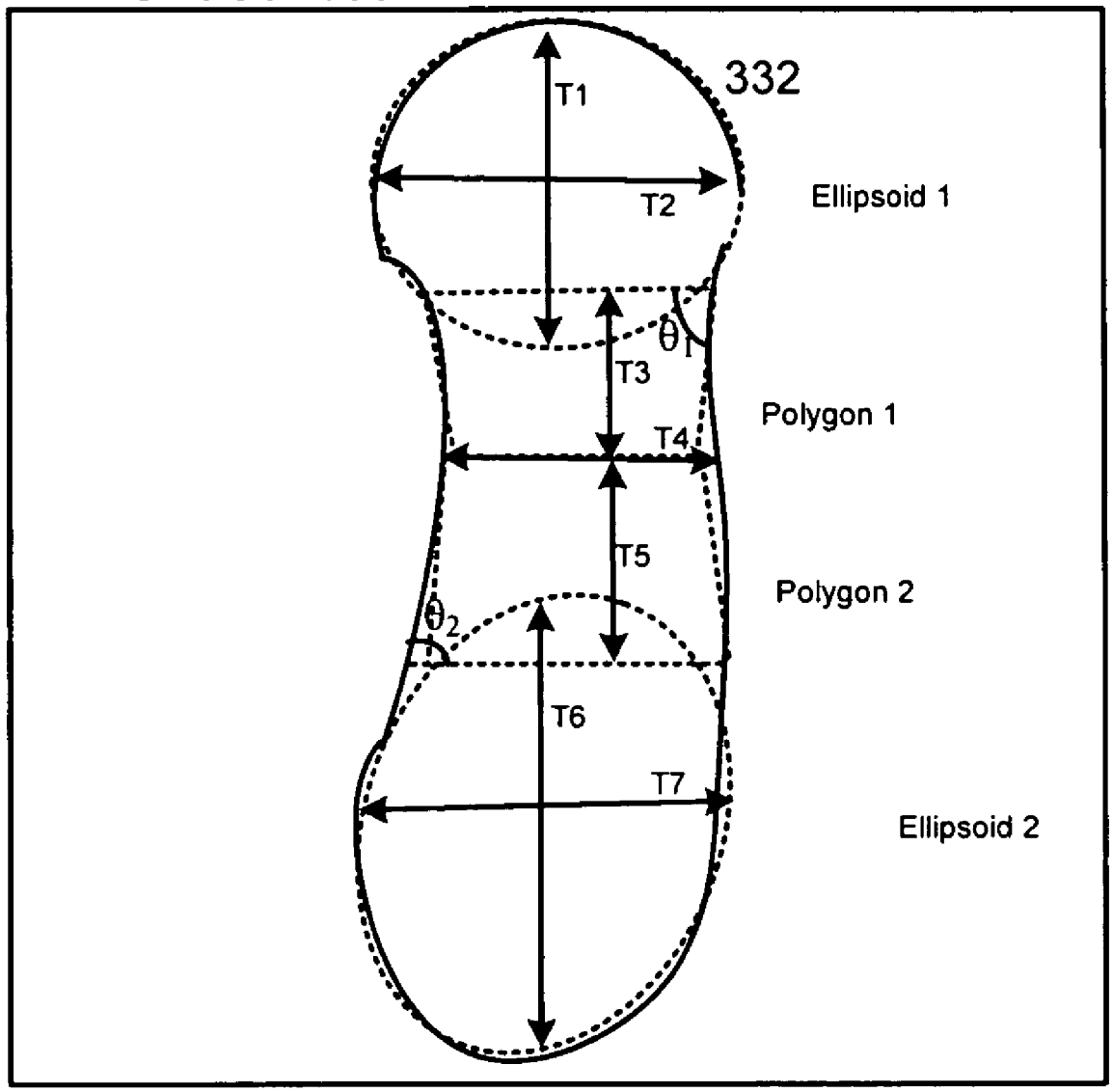
FIG. 3C is an exemplary technique for characterizing the top-view of a two-dimension repeating structure.

FIG. 3C is an exemplary technique for characterizing the top-view of a two-dimension repeating structure. A unit cell 330 of a repeating structure is a feature 332, an island with a peanut-shape viewed from the top. One modeling approach includes approximating the feature 332 with a variable number or combinations of ellipses and polygons. Assume further that after analyzing the variability of the top-view shape of the feature 322, it was determined that two ellipses, Ellipsoid 1 and Ellipsoid 2, and two polygons, Polygon 1 and Polygon 2 were found to fully characterize feature 332. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; T6 and T7 for Ellipsoid 2. Many other combinations of shapes could be used to characterize the top-view of the feature 332 in unit cell 330. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, which is incorporated in its entirety herein by reference.

6. Consecutive Measurement

Figure 4A:
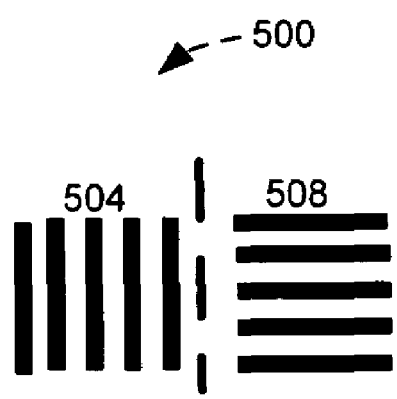
FIGS. 4A, 4B, and 4C are exemplary architectural diagram of the top-view of measurement structures for consecutive measurements of diffraction signals using reflectometric measurements.
Figure 4B:
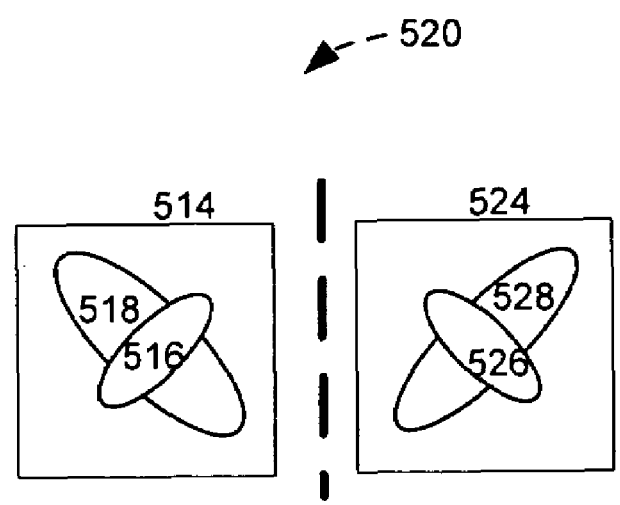
Figure 4C:
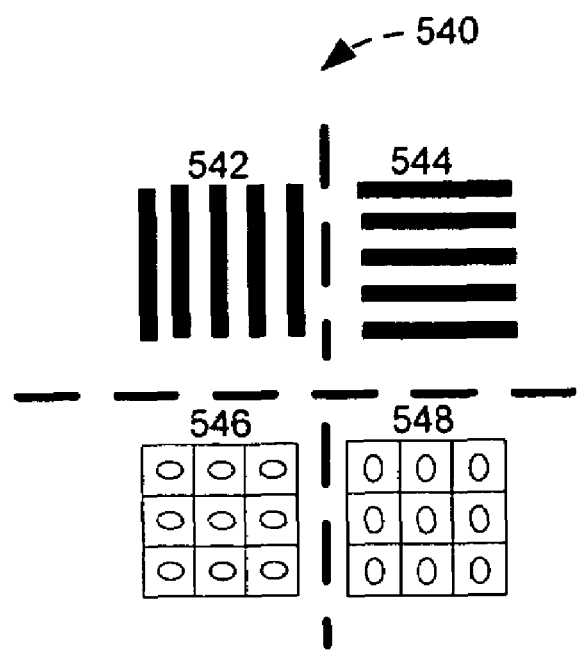

The typical sequence of steps for optical metrology measurements of structures include loading the wafer, positioning the optical metrology device to the measurement site by either moving the measurement head or the wafer, alignment of the illumination beam to the measurement structure, performing the measurement, and unloading the wafer. FIGS. 4A, 4B, and 4C are exemplary architectural diagrams of the top-views of measurement structures for consecutive measurements of diffraction signals using reflectometric measurements. The arrangement of the measurement structures depicted in FIGS. 4A, 4B, and 4C facilitate measuring the measurement structures consecutively, thereby eliminating the steps of loading and reloading the wafer for subsequent measurements.

Referring to FIG. 4A, the measurement structures 500 include a vertical line and space repeating structure 504 and a horizontal line and space repeating structure 508. Repeating structure 508 is formed abutting repeating structure 504. Repeating structure 508 is formed to have the same features as repeating structure 504 but rotated about 90 degrees. Repeating structures 504 and 508 may be in different layers in a multi-layer structure, such as those in chemical-mechanical planarization (CMP) layers.

In the present exemplary embodiment, a polarized reflectometer is used to measure diffraction signals of repeating structures 504, 508. A first diffraction signal can be measured of repeating structure 504 using the polarized reflectometer. A second diffraction signal can be measured of repeating structure 508 using the polarized reflectometer. A typical reflectometer at zero angle of incidence (AOI), i.e., normal AOI, may be used to measure repeating structures 504 and 508. However, it is understood that reflectometers with a non-normal incidence illumination beam may be used.

The first and second measured diffraction signals are measured consecutively. Thus, in the present exemplary embodiment, the second measured diffraction signal is measured without unloading and reloading the semiconductor wafer after the first measured diffraction signal is measured. Also, the second measured diffraction signal is measured without measuring another diffraction signal of another structure after the first measured diffraction signal is measured.

The first measured diffraction signal is compared to a first simulated diffraction signal generated using a profile model of the first structure. As described above, the profile model includes profile parameters that characterize geometries of the first structure.

One or more features of the first structure are determined based on the comparison of the first measured diffraction signal to the first simulated diffraction signal. In particular, as described above, a library-based or regression-based process can be used to determine one or more features of the first structure based on the comparison of the first measured diffraction signal to the first simulated diffraction signal.

In the present exemplary embodiment, the second measured diffraction signal is converted to a converted diffraction signal. The converted diffraction signal can be calculated as the negative of the second measured diffraction signal as shown below:

$$S_2 = -(S_1) \qquad 1.01.$$

$S_1$ is the second measured diffraction signal. $S_2$ is the converted diffraction signal.

The converted diffraction signal is compared to the first simulated diffraction signal or a second simulated diffraction signal generated using the same profile model as the first simulated diffraction signal. In particular, if the converted diffraction signal and the first simulated diffraction signal do not match within a matching criterion, the converted diffraction signal can be compared to the second simulated diffraction signal.

One or more features of the second structure are determined based on the comparison of the converted diffraction signal to the first or second simulated diffraction signal. In particular, as described above, a library-based or regression-based process can be used to determine one or more features of the first structure based on the comparison of the converted diffraction signal to the first or second simulated diffraction signal.

When a library-based process is used to determine the one or more features of the first and second structures, the first and second simulated diffraction signals are obtained from a library of simulated diffraction signals. In the present exemplary embodiment, by converting the second measured diffraction signal to a converted diffraction signal, one library of simulated diffraction signals can be used for the comparison of the first measured diffraction signal and the converted diffraction signal. Thus, the simulated diffraction signals in the library of simulated diffraction signals were generated using the same profile model for the first and second structures. As described above, to generate the simulated diffraction signals in the library, the profile parameters of the profile model are varied to generate a set of hypothetical profiles. The simulated diffraction signals are generated using the set of hypothetical profiles.

When a regression-based process is used to determine the one or more features of the first and second structures, the first and second simulated diffraction signals are generated during the regression process using the same profile model. In particular, a first hypothetical profile is generated using a first setting of profile parameters of the profile model. The first simulated diffraction signal is generated using the first hypothetical profile. In determining one or more features of the second structure, if the converted diffraction signal and the first simulated diffraction signal do not match within a matching criterion, a second hypothetical profile is generated using a second setting of profile parameters of the profile model, where the second setting of profile parameters is different than the first setting. The second simulated diffraction signal is generated using the second hypothetical profile. The converted diffraction signal is then compared to the second simulated diffraction signal.

Referring to FIG. 4B, the measurement structures 520 comprises two repeating structures where only one unit cell each 514 and 524 of the repeating structures are shown. Unit cell 514 depicts a top-view of an elliptical post 516 over an elliptical island 518. The major axis of the elliptical island 518 is larger than the major axis of the post 516 and the major axis of the elliptical island 518 is about 45 degrees from a vertical position. Unit cell 524 is similar to unit cell 514 except that unit cell 524 is rotated 90 degrees clockwise compared to unit cell 514B. As mentioned above, a polarized reflectometer is used to measure the repeating structures of the measurement structures 520. One or more features of measurement structures 520 can be determined as described above.

FIG. 4C depicts two pairs of measurement structures 540. Repeating structure 542 is similar to repeating structure 504 in FIG. 4A, i.e., a repeating structure of vertical lines and spaces. Repeating structure 544 is similar to repeating structure 508 in FIG. 4A (i.e., a repeating structure of horizontal lines and spaces), and repeating structure 542 is similar to repeating structure 504 in FIG. 4A (i.e., a repeating structure of vertical lines and spaces). Repeating structure 546 is a repeating structure of contact holes in orthogonal unit cells, where the contact holes are in the shape of ellipses substantially located in the center of the orthogonal unit cells, with the major axis of the ellipse in a horizontal position. Repeating structure 548 is a repeating structure of contact holes in orthogonal unit cells, where the contact holes are also in the shape of ellipses substantially located in the center of the unit cells, with the major axis of the ellipse in a vertical position. These measurement structures may be measured consecutively in any order. It should be understood that any one or more pairs of measurement structures that are fabricated can be consecutively measured.

As mentioned above, one, two or more pairs of measurement structures fabricated in contiguous areas in the wafer may be measured in a consecutive manner using a sequencing method such as clockwise or counter clockwise. However, it should be noted that any algorithm that minimizes the positioning the optical metrology device to the measurement site by either moving the measurement head or the wafer can be used as well.

Figure 5:
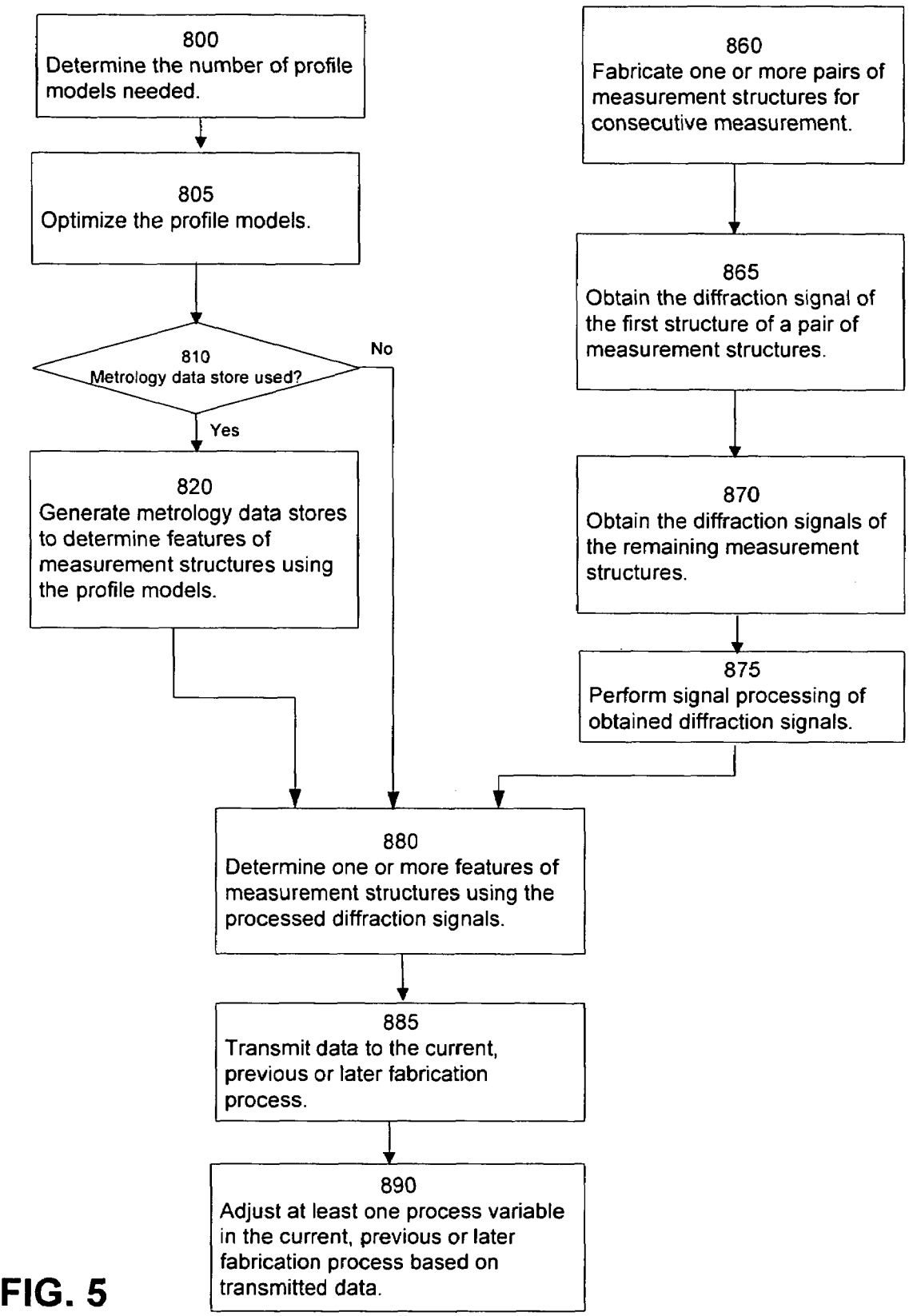
FIG. 5 is an exemplary flowchart for an integrated optical metrology process of using a profile model.

FIG. 5 is an exemplary flowchart for an integrated optical metrology process of using a profile model for determining one or more features of measurement structures fabricated for consecutive measurement and using the one or more determined features for automated process control. In step 800, based on the type of optical metrology tool to be used, the number of profile models is determined. In particular, as mentioned above, when a polarized reflectometer is used, one profile model is used for examining both structures 504 and 508.

In the present exemplary embodiment, in step 805, the profile models determined in step 800 are optimized. In some applications, step 805 can be omitted. Thus, the following steps can be performed using the profile model without optimizing it. For a detailed description of modeling of one-dimension repeating structures, refer to U.S. patent application Ser. No. 10/206,291, OPTIMIZED MODEL AND PARAMETER SELECTION FOR OPTICAL METROLOGY, by Vuong, et al., filed on Jun. 27, 2002, and is incorporated in its entirety herein by reference. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference.

In step 810, if a metrology data store is determined to be desired by the application, a metrology data store is generated for each profile model. Typically, a metrology data store is desired if measurement of the structure is done using an integrated metrology device in a wafer fabrication cluster unit such as a track or etcher. A metrology data store is typically not desired if determination of the one or more features of the measurement structures is done in real time or is done utilizing the regression method mentioned above. If a metrology data store is not desired by the application, then processing proceeds to step 880. Otherwise, in step 820, one or more metrology data stores are generated for each profile model.

Typically, the metrology data store comprises a table, a library or a trained machine learning system (MLS). A table or a library includes pairs of simulated diffraction signal and associated profile parameters. For a more detailed description of a library-based process, see U.S. Pat. No. 6,943,900, titled GENERATION OF A LIBRARY OF PERIODIC GRATING DIFFRACTION SIGNALS, filed on Jul. 16, 2001, issued on Sep. 13, 2005, which is incorporated herein by reference in its entirety. A trained MLS is created to generate a profile or a set of profile parameters based on input measured diffraction signal. For a more detailed description of a generating and using a trained MLS, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In the present exemplary embodiment, independent of steps 800 to 820, in step 860, one or more pairs of measurement structures are fabricated for consecutive measurement. Typical uses of consecutive measurements include measurement of structures to determine the astigmatism error, in chemical-mechanical planarization (CMP) where repeating structures may be in different layers such that a structure in a first layer is rotated ninety degrees compared to a second structure in another layer. Astigmatism error is the difference between a value of a feature with the repeating structure in a first orientation relative to the illumination beam and the value of the same feature of the repeating structure at a second orientation relative to the illumination beam. For example, the critical dimension (CD) of a line and space repeating structure with the line in the horizontal position and the CD of the same repeating structure with the line in a vertical position, similar to the layout if the initial layout was rotated 90 degrees.

Still referring to FIG. 5, in step 865, the diffraction signal off the first measurement structure of the first pair of measurement structures is obtained. For example, if there are two pairs of measurement structures such as those depicted in FIG. 4C, any one of the measurement structures 542, 544, 546 or 548 may be designated as the first measurement structure and measured first. In step 870, the diffraction signals off the remaining measurement structures are obtained. Using the above example of the measurement structures depicted in FIG. 4C, if measurement structure 542 was measured first, then the remaining structures, 544, 546, and 548, are measured consecutively.

In the present exemplary embodiment, referring to FIG. 5, in step 875, preliminary processing of the obtained diffraction signals is performed. As mentioned above, when a polarized reflectometer is used, one of the measured diffraction signal is converted to a converted diffraction signal. In particular, a converted diffraction signal for one measured diffraction signal is calculated as the negative of another measured diffraction signal.

Preliminary processing also includes selecting the diffractions signals at wavelengths that will be used in the regression method or the wavelengths used to create the metrology data stores. For example, a library of pairs of profile parameters and simulated diffraction signals may have been generated using only selected wavelengths based on previous experience with the application or prior testing of the profile model while generating the metrology data store. Furthermore, a trained MLS may also have been trained only on data that were obtained based on selected wavelengths. Additional processing of the obtained diffraction signals include signal filtering based on weighting functions as a function of noise in the measured signal, accuracy of the measured signal, and sensitivity of the measured signal. For a more detailed description of applying weighting functions to enhance measured diffraction signals, see U.S. patent application Ser. No. 11/371,752, titled WEIGHTING FUNCTION TO ENHANCE MEASURED DIFFRACTION SIGNALS IN OPTICAL METROLOGY, filed on Mar. 8, 2006, which is incorporated herein by reference in its entirety.

In step 880, one or more features of the measurement structures are determined using a metrology data store or regression. When a metrology data store is used, a best match simulated diffraction signal to the processed diffraction signal obtained from step 875 is determined and the associated profile or set of profile parameters from the table or library is selected. When a trained MLS is used, the processed diffraction signal is input to the trained MLS to generate a profile or a set of profile parameters. As mentioned above, the profile obtained from either the table, library, or trained MLS is presumed to be the same as the profile of the metrology target structure. When the regression method is used, the processed measured diffraction signal off the measurement structure is compared to a simulated diffraction signal generated using a hypothetical profile. The process is iterated if the diffraction signals do not match within preset or matching criteria. For a more detailed description of a regression-based process, see U.S. Pat. No. 6,785,638, titled METHOD AND SYSTEM OF DYNAMIC LEARNING THROUGH A REGRESSION-BASED LIBRARY GENERATION PROCESS, issued on Aug. 31, 2004, which is incorporated herein by reference in its entirety.

In step 885, data on the determined features of the measurement structures are transmitted to the-current, previous, or later fabrication process device. For example, critical dimensions of the measurement structures determined at an etch fabrication cluster are transmitted to the controller of the current etch fabrication cluster, to a previous fabrication device such as a photolithography cluster, or to a later fabrication device such as a deposition cluster. In step 890, at least one process variable in the current, previous, or later fabrication cluster is adjusted based on the transmitted data on the determined features of the measurement structures.

Figure 6:
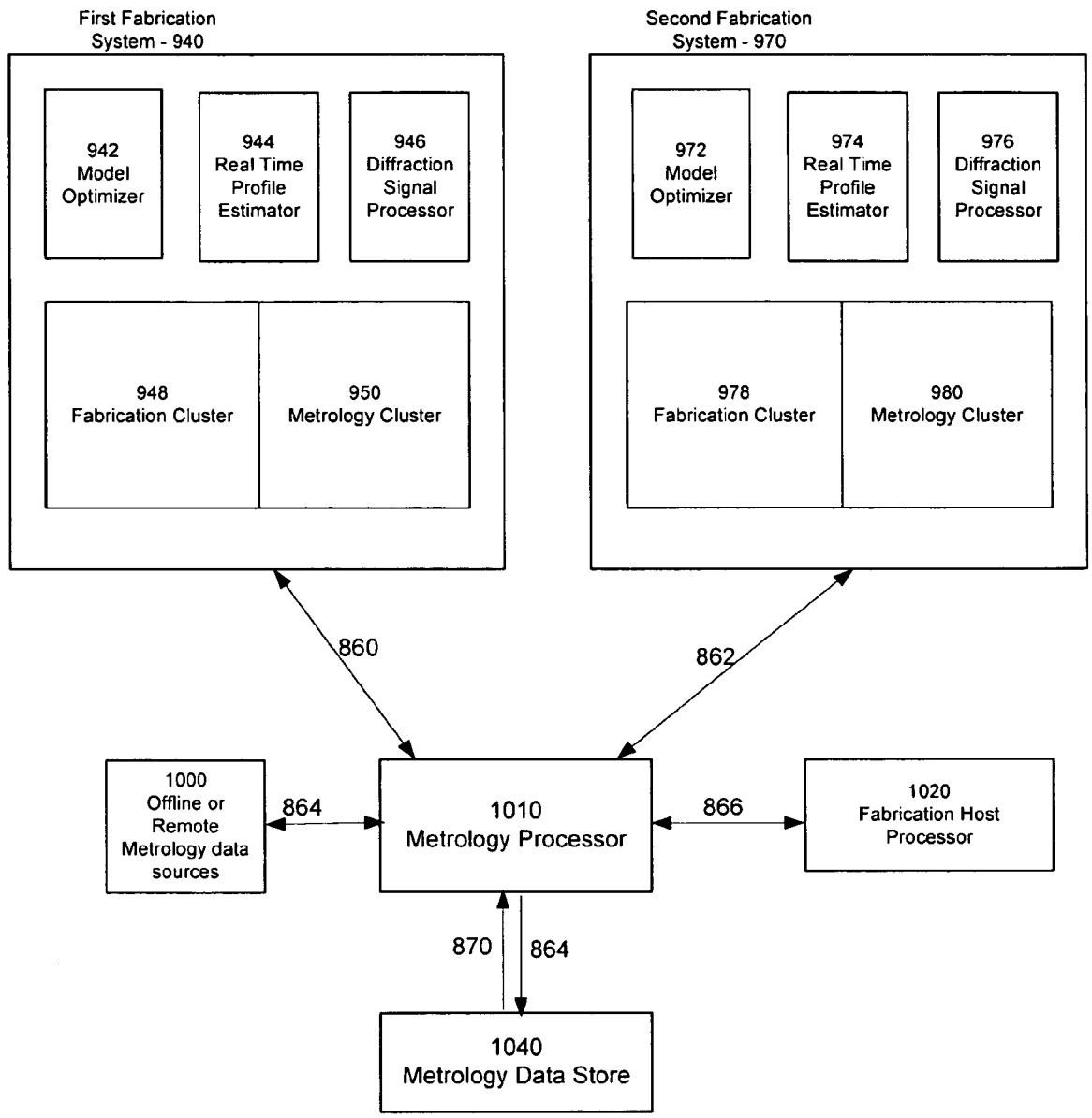
FIG. 6 is an exemplary architectural diagram for linking one or more pairs of fabrication systems with a metrology processor.

FIG. 6 is an exemplary architectural diagram for fabrication cluster systems linked with a metrology processor for determining features of wafer structures and using the features for advanced process control. A first fabrication system 940 includes a model optimizer 942, a real time profile estimator 944, diffraction signal processor 946, a fabrication cluster 948, and a metrology cluster 950. The first fabrication system 940 is coupled to a metrology processor 1010. The metrology processor 1010 is coupled to metrology data sources 1000, a metrology data store 1040, and the fabrication host processors 1020. The model optimizer 942 contains the logic to optimize a profile model of a measurement structure. The real time profile estimator 944 has the logic to determine the best match profile for a measured diffraction signal using regression. The diffraction signal processor 946 utilizes a metrology data store 1040 associated with a measurement structure to determine the best match profile for a measured diffraction signal, and the like. The fabrication cluster 948 may be a track, etcher, deposition process tool. The metrology cluster 950 comprises a set of metrology tools such as polarized reflectometers, spectroscopic ellipsometers, and the like. The second fabrication system 970 includes a model optimizer 972, a real time profile estimator 974, diffraction signal processor 976, a fabrication cluster 978, and a metrology cluster 980 and these devices have the same functions as the equivalent devices in the first fabrication system 940. The first and second fabrication systems, 940 and 970, are coupled to metrology processor 1010.

Referring to FIG. 6, the metrology processor 1010 receives metrology data 864 from the offline or remote metrology data sources 1000. The offline metrology data sources 1000 may be an offline cluster of metrology devices in the fabrication site such as reflectometers, ellipsometers, SEM's and the like. The remote metrology data sources 1000 may include a remote data server or remote processor or website that provides metrology data for the application. Data 860 from the first fabrication system 940 to the metrology processor 1010 may include the profile parameter ranges of the profile model and the generated data stores to determine the structure features. The data stores 1040 may include a library of pairs of simulated diffraction signals and corresponding sets of profile parameters or a trained MLS system that can generate a set of profile parameters for an input measured diffraction signal. Data 870 from data stores 1040 to metrology processor 1010 includes a set of profile parameters and/or simulated diffraction signal. Data 864 from the metrology processor 1010 to metrology data store 1040 includes values of the profile parameters, material refraction parameters, and metrology device parameters in order to specify the portion of the data space to be searched in the library or trained MLS store in the metrology data store 1040. Data 862 transmitted to and from the second fabrication system 970 to the metrology processor 1010 are similar to the data 860 transmitted to and from the first fabrication system 940.

Still referring to FIG. 6, data 866 transmitted to and from the metrology processor 1010 to the fabrication host processor 1020 may include data related to the application recipe and process data measured by the metrology clusters 950 and 980, in the first and second fabrication systems 940 and 970. The metrology data store 1040 in FIG. 6 is the repository of metrology data and the metrology data is made available to the first and/or the second fabrication system 940 and 970. As mentioned above, the first and/or second fabrication system 940 and 970 may include one or more of a photolithography, etch, thermal processing system, metallization, implant, chemical vapor deposition, chemical mechanical polishing, or other fabrication unit.

Data on the features of the measurement structures determined by the real time profile estimator 944 or diffraction signal processor 946 in the first fabrication system 940 may be transmitted to the fabrication host processor 1020. The data can be used by the fabrication host processor to adjust a process variable in the fabrication cluster 948 of the first fabrication system 940 or adjust a process variable in the fabrication cluster 978 of the second fabrication system 970. For example, if the fabrication cluster 948 is a photolithography unit and the fabrication cluster 978 is an etch unit, the data may be top critical dimension of a measurement structure measured by the metrology cluster 950. The value of the top critical dimension may be used by the fabrication host processor 1020 to adjust the focus or exposure of the photolithography unit. Furthermore, the value of the top critical dimension may be used by the fabrication host processor 1020 to adjust an etch variable such as flow rate of the etchant. In a similar manner, the value of a profile parameter of a measurement structure measured by the metrology cluster 980 and determined by the real time profile estimator 974 or the profile server 976 of the second fabrication system 970 may be transmitted to the fabrication host processor 1020. The value of the profile parameter can be used by the fabrication host processor to adjust a process variable in the fabrication cluster 948 of the first fabrication system 940 or adjust a process variable in the fabrication cluster 978 of the second fabrication system 970. It is understood that the second fabrication system may include any fabrication cluster involved in the wafer manufacturing process.

In particular, it is contemplated that functional implementation of the present invention described herein may be implemented equivalently in hardware, software, firmware, and/or other available functional components or building blocks. For example, the metrology data store may be in computer memory or in an actual computer storage device or medium. Other variations and embodiments are possible in light of above teachings, and it is thus intended that the scope of invention not be limited by this Detailed Description, but rather by Claims following.

We claim:

1. A method of examining structures formed on a semiconductor wafer using consecutive measurements, the method comprising;
    forming a first structure on a semiconductor wafer;
    forming a second structure abutting the first structure;
    measuring a first measured diffraction signal of the first structure using a polarized reflectometer;
    measuring a second measured diffraction signal of the second structure using the polarized reflectometer, wherein the first and second measured diffraction signals are measured consecutively;
    comparing the first measured diffraction signal to a first simulated diffraction signal generated using a profile model of the first structure, the profile model having profile parameters that characterize geometries of the first structure;
    determining one or more features of the first structure based on the comparison of the first measured diffraction signal to the first simulated diffraction signal;
    converting the second measured diffraction signal to a converted diffraction signal without similarly converting the first measured diffraction signal;
    comparing the converted diffraction signal to the first simulated diffraction signal or a second simulated diffraction signal generated using the same profile model as the first simulated diffraction signal; and
    determining one or more features of the second structure based on the comparison of the converted diffraction signal to the first or second simulated diffraction signal.

2. The method of claim 1, wherein converting the second measured diffraction signal comprises calculating a negative of the second measured diffraction signal.

3. The method of claim 1, wherein the second structure is formed to have the same features as the first structure rotated about 90 degrees.

4. The method of claim 3, wherein the first and second structures are repeating line and space structures, wherein the lines of the first structure are oriented at about 90 degrees relative to the lines of the second structure.

5. The method of claim 3, wherein the first and second structures have profiles that vary in two dimensions and characterized using unit cells, wherein the unit cell of the first structure is oriented at about 90 degrees relative to the unit cell of the second structure.

6. The method of claim 1, wherein the second measured diffraction signal is measured without unloading and reloading the semiconductor wafer after the first measured diffraction signal is measured.

7. The method of claim 6, wherein the second measured diffraction signal is measured without measuring another diffraction signal of another structure after the first measured diffraction signal is measured.

8. The method of claim 1, further comprising:
    obtaining the first simulated diffraction signal from a library of simulated diffraction signals before comparing the first measured diffraction signal to the first simulated diffraction signal; and
    obtaining the second simulated diffraction signal from the library of simulated diffraction signals before comparing the converted diffraction signal to the second simulated diffraction signal, wherein the simulated diffraction signals in the library of simulated diffraction signals were generated using one profile model for the first and second structures.

9. The method of claim 8, wherein profile parameters of the one profile model for the first and second structures were varied to generate a set of hypothetical profiles, and wherein the simulated diffraction signals in the library of simulated diffraction signals were generated using the set of hypothetical profiles.

10. The method of claim 1, wherein comparing the converted diffraction signal comprises:
    comparing the converted diffraction signal to the first simulated diffraction signal;
    if the converted diffraction signal and the first simulated diffraction signal do not match within a matching criterion:
        generating a hypothetical profile by adjusting one or more profile parameters of the profile model; and
        generating the second simulated diffraction signal using the hypothetical profile.

11. The method of claim 1 further comprising:
    transmitting data on the one or more determined features of the first or second structure to a metrology processor.

12. The method of claim 11, wherein the transmitted data is used to alter at least one process variable in fabrication device.

13. A method of examining structures formed on a semiconductor wafer using consecutive measurements, the method comprising;
    obtaining a first measured diffraction signal of a first structure formed on the semiconductor wafer, the first measured diffraction signal measured using a polarized reflectometer;
    obtaining a second measured diffraction signal of a second structure formed abutting the first structure, the second measured diffraction signal measured using the polarized reflectometer, wherein the first and second measured diffraction signals are measured consecutively;
    comparing the first measured diffraction signal to a first simulated diffraction signal generated using a profile model of the first structure, the profile model having profile parameters that characterize geometries of the first structure;
    determining one or more features of the first structure based on the comparison of the first measured diffraction signal to the first simulated diffraction signal;
    converting the second measured diffraction signal to a converted diffraction signal without similarly converting the first measured diffraction signal;

comparing the converted diffraction signal to the first simulated diffraction signal or a second simulated diffraction signal generated using the same profile model as the first simulated diffraction signal; and determining one or more features of the second structure based on the comparison of the converted diffraction signal to the first or second simulated diffraction signal.

14. The method of claim 13, wherein converting the second measured diffraction signal comprises calculating a negative of the second measured diffraction signal.

15. The method of claim 13, further comprising:
obtaining the first simulated diffraction signal from a library of simulated diffraction signals before comparing the first measured diffraction signal to the first simulated diffraction signal; and
obtaining the second simulated diffraction signal from the library of simulated diffraction signals before comparing the converted diffraction signal to the second simulated diffraction signal, wherein the simulated diffraction signals in the library of simulated diffraction signals were generated using one profile model for the first and second structures.

16. The method of claim 15, wherein profile parameters of the one profile model for the first and second structures were varied to generate a set of hypothetical profiles, and wherein the simulated diffraction signals in the library of simulated diffraction signals were generated using the set of hypothetical profiles.

17. The method of claim 13, wherein comparing the converted diffraction signal comprises:
comparing the converted diffraction signal to the first simulated diffraction signal;
if the converted diffraction signal and the first simulated diffraction signal do not match within a matching criterion:
generating a hypothetical profile by adjusting one or more profile parameters of the profile model; and
generating the second simulated diffraction signal using the hypothetical profile.

18. The method of claim 13 further comprising:
transmitting data on the one of more determined features of the first or second structure to a metrology processor.

19. The method of claim 18, wherein the transmitted data is used to alter at least one process variable in fabrication device.

20. A computer-readable storage medium having computer-executable instructions for examining structures formed on a semiconductor wafer using consecutive measurements, comprising instructions for;
obtaining a first measured diffraction signal of a first structure formed on the semiconductor wafer, the first measured diffraction signal measured using a polarized reflectometer;
obtaining a second measured diffraction signal of a second structure formed abutting the first structure, the second measured diffraction signal measured using the polarized reflectometer, wherein the first and second measured diffraction signals are measured consecutively;
comparing the first measured diffraction signal to a first simulated diffraction signal generated using a profile model of the first structure, the profile model having profile parameters that characterize geometries of the first structure;

determining one or more features of the first structure based on the comparison of the first measured diffraction signal to the first simulated diffraction signal;
converting the second measured diffraction signal to a converted diffraction signal without similarly converting the first measured diffraction signal;
comparing the converted diffraction signal to the first simulated diffraction signal or a second simulated diffraction signal generated using the same profile model as the first simulated diffraction signal; and
determining one or more features of the second structure based on the comparison of the converted diffraction signal to the first or second simulated diffraction signal.

21. The computer-readable storage medium of claim 20, wherein converting the second measured diffraction signal comprises calculating a negative of the second measured diffraction signal.

22. A system to examine structures formed on a semiconductor wafer using consecutive measurements, the system comprising;
a polarized reflectometer configured to:
measure a first diffraction signal of a first structure formed on the semiconductor wafer; and
measure a second diffraction signal of a second structure formed abutting the first structure, wherein the first and second measured diffraction signals are measured consecutively; and
a metrology processor configured to:
obtain the first measured diffraction signal;
compare the first measured diffraction signal to a first simulated diffraction signal generated using a profile model of the first structure, the profile model having profile parameters that characterize geometries of the first structure;
determine one or more features of the first structure based on the comparison of the first measured diffraction signal to the first simulated diffraction signal;
obtain the second measured diffraction signal;
convert the second measured diffraction signal to a converted diffraction signal without similarly converting the first measured diffraction signal;
compare the converted diffraction signal to the first simulated diffraction signal or a second simulated diffraction signal generated using the same profile model as the first simulated diffraction signal; and
determine one or more features of the second structure based on the comparison of the converted diffraction signal to the first or second simulated diffraction signal.

23. The system of claim 22, further comprising:
a fabrication cluster configured to form the first and second structures on the semiconductor wafer.

24. The system of claim 23, wherein the metrology processor is further configured to:
transmit data on the one of more determined features of the first or second structure to a current, previous, or later fabrication cluster.

25. The system of claim 24, wherein the transmitted data is used to alter a process variable in the current, previous, or later fabrication clusters.

26. The system of claim 22, wherein converting the second measured diffraction signal comprises calculating a negative of the second measured diffraction signal.

* * * * *